(12) United States Patent
Erkens et al.

(10) Patent No.: US 11,129,779 B2
(45) Date of Patent: Sep. 28, 2021

(54) THICKENING SYSTEM IN A PERCARBONATE-CONTAINING BLONDING AGENT

(71) Applicant: Henkel AG & Co. KGaA, Duesseldorf (DE)

(72) Inventors: Udo Erkens, Willich (DE); Torsten Lechner, Langenfeld (DE)

(73) Assignee: HENKEL IP & HOLDING GMBH, Duesseldorf (DE)

( * ) Notice: Subject to any disclaimer, the term of this patent is extended or adjusted under 35 U.S.C. 154(b) by 0 days.

(21) Appl. No.: 16/721,904

(22) Filed: Dec. 19, 2019

(65) Prior Publication Data

US 2020/0206100 A1    Jul. 2, 2020

(30) Foreign Application Priority Data

Dec. 28, 2018 (DE) .................... 10 2018 133 685.3
Feb. 28, 2019 (DE) .................... 10 2019 105 162.2

(51) Int. Cl.
| | | |
|---|---|---|
| *A61Q 5/08* | (2006.01) | |
| *A61K 8/19* | (2006.01) | |
| *A61K 8/73* | (2006.01) | |
| *A61K 8/23* | (2006.01) | |
| *A61K 8/44* | (2006.01) | |

(52) U.S. Cl.
CPC ............... *A61K 8/19* (2013.01); *A61K 8/23* (2013.01); *A61K 8/44* (2013.01); *A61K 8/73* (2013.01); *A61K 8/731* (2013.01); *A61Q 5/08* (2013.01); *A61K 2800/87* (2013.01)

(58) Field of Classification Search
CPC ... A61Q 5/08; A61K 8/22; A61K 8/44; A61K 8/46; A61K 8/731; A61K 8/25; A61K 8/365; A61K 8/73; A61K 2800/48
USPC ............................................... 424/62
See application file for complete search history.

(56) References Cited

U.S. PATENT DOCUMENTS

| | | |
|---|---|---|
| 10,137,067 B2 | 11/2018 | Mueller |
| 2013/0284199 A1* | 10/2013 | Wood ............ A61Q 5/10 132/208 |
| 2014/0082854 A1* | 3/2014 | Landa ............ G01N 33/4833 8/405 |
| 2019/0000732 A1 | 1/2019 | Wang et al. |
| 2019/0175463 A1 | 6/2019 | Erkens et al. |

FOREIGN PATENT DOCUMENTS

| | | |
|---|---|---|
| DE | 102014226366 A1 | 6/2016 |
| EP | 2055296 A1 | 5/2009 |
| EP | 2272489 A1 | 1/2011 |

* cited by examiner

*Primary Examiner* — Eisa B Elhilo
(74) *Attorney, Agent, or Firm* — Lorenz & Kopf, LLP

(57) ABSTRACT

The present disclosure relates to blonding agents which serve as a lightening agent for keratinic fibers, in particular human hair. Furthermore, the present disclosure relates to a cosmetic product comprising the blonding agent contained in a packaging impermeable to water vapor. Furthermore, the present disclosure relates to a method for blonding human hair. The blonding agent is an anhydrous, powdered cosmetic composition, wherein the cosmetic composition contains at least one oxidizing compound and a mixture of thickening agents.

14 Claims, No Drawings

US 11,129,779 B2

THICKENING SYSTEM IN A PERCARBONATE-CONTAINING BLONDING AGENT

CROSS-REFERENCE TO RELATED APPLICATION

This application claims priority to German Patent Application No. 10 2019 105 162.2, filed Feb. 28, 2019, and to German Patent Application No. 10 2018 133 685.3, filed Dec. 28, 2018, which are both incorporated herein by reference in their entirety.

TECHNICAL FIELD

The present disclosure relates to blonding agents which serve as a lightening agent for keratinic fibers, in particular human hair. Furthermore, the present disclosure relates to a method for blonding human hair.

BACKGROUND

The blonding agent is an anhydrous, powdered cosmetic composition, wherein the cosmetic composition contains at least one oxidizing compound, at least one percarbonate, and at least one thickening agent.

The lightening of one's own hair has always been the desire of many consumers, since a blond hair color is considered attractive and fashionable in terms of desirability. Various blonding agents having different blonding performance are available in the market for this purpose. The oxidizing agents contained in these products are able to lighten the hair fiber by the oxidative destruction of the hair's own melanin. For a moderate blonding effect, the use of hydrogen peroxide, optionally with the use of ammonia or other alkalizing agents, is sufficient as the oxidizing agent alone. To achieve a stronger blonding effect, a mixture of hydrogen peroxide and at least one compound selected from percarbonates and persalts, in particular peroxodisulfate salts and/or peroxomonosulfate salts, is usually used. To enhance the blonding effect, the agents contain higher use concentrations of hydrogen peroxide and percarbonates or persalts, in particular persulfates. Dark, dark brown or black hair can be lightened in one step by from about 4 to about 6 shades. The hydrogen peroxide and the percarbonates or persalts are kept separate from each other until use so as not to prematurely deactivate the percarbonates or persalts. The hydrogen peroxide component, which comprises an aqueous solution of hydrogen peroxide, has an acidic pH value, in particular a pH value of from about 2.5 to about 5.5, in particular from about 3 to about 5, for the stabilization of the hydrogen peroxide, in each case measured at 20° C.

For the melanin degrading effect of the hydrogen peroxide and the blonding action on the keratinic fiber, however, it is advantageous when the application mixture of hydrogen peroxide solution and persalt has an alkaline pH value, preferably lying in the range of from about 8 to about 12, particularly preferably in the range of from about 8.5 to about 11.5, most preferably in the range of from about 9 to about 10.5, each measured at 20° C.

There are several possibilities for setting an alkaline pH value of the lightening application mixture:

The blonding agent contains, in addition to the at least one persalt or optionally also percarbonate, at least one powdered alkalizing agent in such a total amount that the application mixture has the desired alkaline pH value; or the hydrogen peroxide solution is combined not only with the blonding agent but additionally with an alkalizing agent formulation for the application mixture.

If the alkalizing agent preparation and/or the blonding agent are added to oxidation dye precursors and/or direct acting dyes, the hair can be dyed at the same time. Corresponding 3-component hair coloring agents are offered in particular for consumers with very dark melanin-rich hair.

At least two separately packaged components, the persulfate powder and the hydrogen peroxide solution, must therefore be mixed with one another for the preparation of the ready-to-use blonding agent. The user who consumes as sustainably as possible is also increasingly paying attention to the ecological aspects of a product. One goal here also is the economization of packaging material. Products that are used in as concentrated a form as possible, which include only one component and that need only to be optimally mixed with water to produce the application mixture, offer a decisive advantage in terms of the economization packaging material.

As a result, the packages are usually bulky, which impairs the sustainability in matters of environmental and resource conservation. An advantage would be provided when a solid would be used as an oxidizing agent instead of a liquid hydrogen peroxide solution. The bleaching agent components could then also be offered in a container since the reaction of the components only requires mixing with water.

Persulfates and percarbonates are known as solid oxidizing agents for bleaching agents. They are usually used in the prior art as inorganic salts. However, the use of salts is again detrimental to the adjustment of the viscosity of the ready-to-use bleaching agent composition. In fact, polyelectrolytes such as xanthan, which lose their effect of increasing the viscosity with increasing salt content, are often used as thickeners. When the ready-to-use cosmetic agent has too low a viscosity, it can only be applied unfavorably and is therefore less manageable.

BRIEF SUMMARY

Blonding agents for changing the natural color of keratinic fibers and methods for lightening keratinic fibers are provided herein. In an embodiment, a blonding agent for changing the natural color of keratinic fibers includes a cosmetic composition (KM), wherein the cosmetic composition (KM) includes:
  at least one oxidizing compound and
  a mixture of thickening agents,
The mixture of thickening agents comprises a cellulose gum, a hydroxyethyl cellulose, and a xanthan gum.

In another embodiment, a blonding agent for changing the natural color of keratinic fibers is provided. The blonding agent includes a cosmetic composition (KM), wherein the cosmetic composition (KM) includes:
  sodium peroxodisulfate, potassium peroxodisulfate, and ammonium peroxodisulfate in a total amount of from about 30 to about 50% by weight, based on the total weight of the blonding agent;
  at least one percarbonate present in the blonding agent in a total amount of from about 4 to about 12% by weight based on the total weight of the blonding agent; and
  a thickening agent comprising a mixture of cellulose gum in an amount of from about 1.5 to about 3% by weight, of xanthan gum in an amount of from about 2 to about 4% by weight, and of hydroxyethyl cellulose in an amount of from about 1.5 to about 4% by weight, in each case based on the total weight of the blonding agent, wherein the total amount of thickening agents in the blonding agent is from about 6 to about 9% by weight, based on the total weight of the blonding agent.

In another embodiment, a method for lightening keratinic fibers is provided, wherein the blonding agent as described above is mixed with water, the resulting mixture is applied to the keratin-containing fibers immediately after the mixing and is left on the keratin-containing fibers from about 5 to about 60 minutes, then the keratin-containing fibers are rinsed with water and/or are rinsed with water and a surfactant-containing cleaning agent.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object underlying the present disclosure was to provide a blonding agent which shows a good blonding effect with easy and pleasant handling of the blonding agent. Furthermore, the object underlying the present disclosure was to provide a feature for lightening or blonding keratinic fibers, in particular human hair, which damages the keratin fibers as little as possible and is easy to handle. In particular, the object underlying the present disclosure was to find a blonding agent that can be provided in a space-saving manner and using little packaging material.

The object underlying the present disclosure is solved by the blonding agents as contemplated herein. A first subject of the present disclosure is therefore a blonding agent for changing the natural color of keratinic fibers, in particular human hair, comprising a cosmetic composition (KM), wherein the cosmetic composition (KM) contains
- at least one oxidizing compound and
- a mixture of thickening agents, exemplified in that the mixture of thickening agents comprises a cellulose gum, a hydroxyethyl cellulose and a xanthan gum.

The blonding agent contains thickening agents as an essential ingredient. In the context of the present disclosure, the term "thickening agent" is to be understood to mean compounds which can bind liquids, in particular water, and increase the viscosity of these liquids. In the context of the present disclosure, these also include gelling agents which are capable of thickening liquids to compositions having a gelatinous consistency or to gels.

"Thickening agent" and "thickener" are used synonymously in the context of the present disclosure. As contemplated herein, gel-like cosmetic agents or gels are understood to mean dimensionally stable, easily deformable disperse systems of at least two components, the gelling agent (usually a solid, colloidally divided substance having long or highly branched compounds) and a liquid (usually water) as a dispersion agent. The gelling agent forms a spatial network in the liquid, wherein the individual gel-forming compounds adhere to one another by main and/or minor valences at different spatial points.

It has surprisingly been found that the combination of the thickening agents leads to an easier handling of the blonding agent. When mixing the blonding agent as contemplated herein, which contains the three special thickening agents, with water, the mixture remains at low viscosity in the first few seconds of mixing, so that the mixing can be performed easily and quickly. The viscosity then increases and can be easily applied to the keratinic fibers due to the higher viscosity. A maximum viscosity is achieved after the usual time required for mixing and application. The then already applied mixture does not drip from the hair. The advantages of improved handleability of the blonding agent as contemplated herein are thus obtained due to the slow increase in viscosity achieved by the use of thickening agents.

It has proved, as described above, a special challenge to prepare a cosmetic agent for lightening hair which uses solid substances as the oxidizing agent and no liquid hydrogen peroxide solution as a component and which at the same time comprises a thickener which advantageously adjusts the viscosity of the ready-to-use cosmetic composition. The problem is that thickening agents, which constitute polyelectrolytes, lose their viscosity-increasing properties with increasing salt content. It has surprisingly proved to be advantageous when the mixture of three thickening agents is used as a thickening agent.

It is particularly advantageous when the amount of thickening agent is relatively large. The ready-to-use cosmetic agent is advantageously handled as a result.

Intensive investigations have surprisingly shown that a mixture of three thickening agents is particularly well suited to achieve the advantageous effect in terms of viscosity. A particularly preferred embodiment of the present disclosure therefore relates to a blonding agent that contains a mixture of a cellulose gum, a hydroxyethyl cellulose and a xanthan gum, wherein preferably the amount of cellulose gum is from about 1 to about 5% by weight, preferably from about 1.5 to about 3% by weight, the amount of xanthan gum is from about 1 to about 6% by weight, preferably from about 2 to about 4% by weight, and/or the amount of hydroxyethyl cellulose is from about 1 to about 5% by weight, preferably from about 1.5 to about 4% by weight, in each case based on the total weight blonding agent.

According to a preferred embodiment of the present disclosure, the total amount of thickening agent in the blonding agent is from about 1 to about 15% by weight, preferably from about 3 to about 13% by weight, more preferably from about 5 to about 11% by weight, most preferably from about 6 to about 9% by weight, based on the total weight of the blonding agent. Within these limits, the above-mentioned beneficial effects achieved by mixing the thickening agents are best achieved. The following amounts of thickening agent are more preferably used in the blonding agents as contemplated herein: The mixture of thickening agents contains cellulose gum in an amount of from about 1 to about 5% by weight, preferably from about 1.5 to about 3% by weight, xanthan gum in an amount of from about 1 to about 6% by weight, preferably from about 2 to about 4% by weight, and/or hydroxyethylcellulose in an amount of from about 1 to about 5% by weight, preferably from about 1.5 to about 4% by weight, in each case based on the total weight of the blonding agent.

The blonding agent as contemplated herein contains at least one oxidizing compound as a further essential constituent. In the context of the present disclosure, the terms "oxidizing compound" and "oxidizing agent" are to be used synonymously. The oxidizing agent is preferably an oxidizing agent which is solid at 20° C. and $10^5$ Pa, in particular a powdered oxidizing agent. The oxidizing agent causes the blonding of the keratinic fibers.

According to a preferred embodiment of the present disclosure, the blonding agent contains, as an oxidizing compound, a percarbonate, preferably an alkali metal, alkaline earth metal or ammonium salt of a percarbonate, in particular sodium percarbonate. The percarbonate, in particular the sodium percarbonate, is preferably present in the blonding agent in a total amount of from about 2 to about 14% by weight, more preferably from about 4 to about 12% by weight, yet more preferably from about 6 to about 10% by weight, based on the total weight of the blonding agent.

As contemplated herein, preference is thus given to using percarbonates, such as sodium percarbonate. Sodium percarbonates are understood to mean sodium carbonate-hydrogen peroxide complexes. Commercially available sodium percarbonate has the average composition 2 $Na_2CO_3 \cdot 3\, H_2O_2$. Sodium percarbonate is present as a white, water-soluble powder which readily decomposes into sodium carbonate and bleaching and oxidizing "active" oxygen. A preferred blonding agent can thus be used without free hydrogen peroxide.

According to a preferred embodiment of the present disclosure, the cosmetic agent is free of hydrogen peroxide. By this it is meant that the cosmetic agent is substantially free of a liquid hydrogen peroxide-containing solution, in particular it is meant that no hydrogen peroxide in liquid form or in a liquid solution is added to the blonding agent during the formulation. Of course, traces of water can be present in the blonding agent, which traces produce hydrogen peroxide upon reaction with the percarbonate. However, this should only result in a small amount of free hydrogen peroxide. Hydrogen peroxide can of course also be present formally in the empirical formula of the solid oxidizing agent, in the crystal structure of the percarbonate. It is thus also not available as free hydrogen peroxide in the context of the present disclosure.

The use of percarbonates makes it possible to dispense with hydrogen peroxide. Packaging material can thus be saved. The percarbonates are solids at ambient conditions which can be provided together with the remaining components in a packaging. The blonding agent is stable in storage in the combination of substances. The blonding agent as contemplated herein is mixed with water and constitutes a ready-to-use cosmetic agent for blonding.

Although the agents as contemplated herein are primarily suitable for blonding and lightening keratin-containing fibers, in principle, there is nothing to prevent their use in other fields as well.

According to a preferred embodiment of the present disclosure, the oxidizing compound is a mixture of a percarbonate, in particular sodium percarbonate, and one or more inorganic salts of a peroxosulphuric acid, wherein the inorganic salt of a peroxosulphuric acid is preferably selected from the group of sodium peroxodisulfate, potassium peroxodisulfate, ammonium peroxodisulfate, sodium peroxomonosulfate, potassium peroxomonosulfate, ammonium peroxomonosulfate, and mixtures of these inorganic salts of peroxosulfuric acid, more preferably mixtures of potassium peroxodisulfate and ammonium peroxodisulfate or mixtures of sodium peroxodisulfate and ammonium peroxodisulfate, wherein more preferably the total amount of inorganic salt of a peroxodisulfuric acid is from about 10 to about 70% by weight, more preferably from about 20 to about 50% by weight, yet more preferably from about 25 to about 45% by weight, most preferably from about 30 to about 40% by weight, in each case based on the total weight of the blonding agent.

Peroxosulfuric acids are understood to mean peroxodisulfuric acid and peroxomonosulfuric acid (Caro's acid).

According to a preferred embodiment of the present disclosure, the at least one inorganic salt of a peroxosulfuric acid is selected from the group of sodium peroxodisulfate, potassium peroxodisulfate, ammonium peroxodisulfate, sodium peroxomonosulfate, potassium peroxomonosulfate and ammonium peroxomonosulfate. Or the inorganic salt of a peroxosulfuric acid comprises mixtures of said inorganic salts of a peroxosulfuric acid, preferably mixtures of potassium peroxodisulfate and ammonium peroxodisulfate or mixtures of sodium peroxodisulfate and ammonium peroxodisulfate. According to the preferred embodiment of the present disclosure, the total amount of inorganic salt of a peroxosulfuric acid is from about 10 to about 70% by weight, more preferably from about 20 to about 50% by weight, still more preferably from about 25 to about 45% by weight, most preferably from about 30 to about 40% by weight, in each case based on the total weight of the blonding agent.

According to a particularly preferred embodiment of the present disclosure, the inorganic salt of a peroxosulfuric acid constitutes a mixture comprising from about 5 to about 40% by weight, preferably from about 10 to about 35% by weight, more preferably from about 15 to about 30% by weight of potassium peroxodisulfate, from about 5 to about 20% by weight, preferably from about 8 to about 18% by weight, more preferably from about 10 to about 15% by weight of ammonium peroxodisulfate and/or from 0 to about 10% by weight, preferably from about 1 to about 9% by weight, more preferably from about 2 to about 6% by weight of sodium perooxodisulfate, in each case based on the total weight of the blonding agent.

The combination of the inorganic salt of a peroxosulfuric acid and the percarbonate in conjunction with the thickening agents is advantageous for the solution of the object underlying the present disclosure. The inorganic salt of peroxosulfuric acid and the percarbonate are in powder form. The components can be packed in a space-saving manner and there is no need to use a liquid hydrogen peroxide solution.

Blonding agents preferred as contemplated herein are powders which preferably have a bulk density in the range of from about 500 to about 1000 g/l (grams/liter), preferably from about 550 to about 900 g/l, particularly preferably from about 600 to about 820 g/l. The determination of the bulk density is preferably carried out according to EN ISO 60 (version 01/2000) or DIN ISO 697 (version 01/1984). As contemplated herein, the term "powder" or "powdered" is to be understood to mean a free-flowing dosage form of individual particles which is solid at 20° C. and $10^5$ Pa, in which the individual particles have particle sizes in the range from about 0.1 µm to a maximum of about 1.6 mm. The determination of the particle sizes can preferably be carried out by employing laser diffraction measurement in accordance with ISO 13320-1 (2009). Optionally, the particles can be adapted in their grain size by physical treatment, such as sieving, pressing, granulating or pelleting, or by the addition of certain excipients, to the requirements of the blonding agent, for example, to enable a better miscibility of the individual powder constituents or the miscibility of the blonding agent with a hydrogen peroxide preparation.

Unless otherwise indicated, state references refer to standard conditions, that is, to a temperature of 25° C. and a pressure of $10^5$ Pa.

In the context of the present disclosure, the use of xanthan, which has a mean particle diameter D50 of from about 140 to about 200 µm and a viscosity (0.3% by weight solution in 0.3% KCl) of from about 250 to about 800 mPas (measured with Brookfield viscometer at 3 rpm), has been shown to be particularly advantageous. Such xanthans are commercially available, for example, under the trade name Keltrol CG-SFT from CP Kelco.

As contemplated herein, the term "xanthans" is understood to mean naturally occurring polysaccharides which can be obtained from sugar-containing substrates with the aid of bacteria of the genus *Xanthomonas*. The xanthan gum d-glucose, d-mannose, d-glucuronic acid, acetate and pyruvate used as contemplated herein preferably contains a molar ratio of about 28:30:20:17:5.1-6.3, wherein the main chain includes β-1,4-linked glucose units (also referred to as a cellulose chain). The xanthans used with particular preference in the context of the present disclosure have the CAS No. 11138-66-2 and the following structural formula

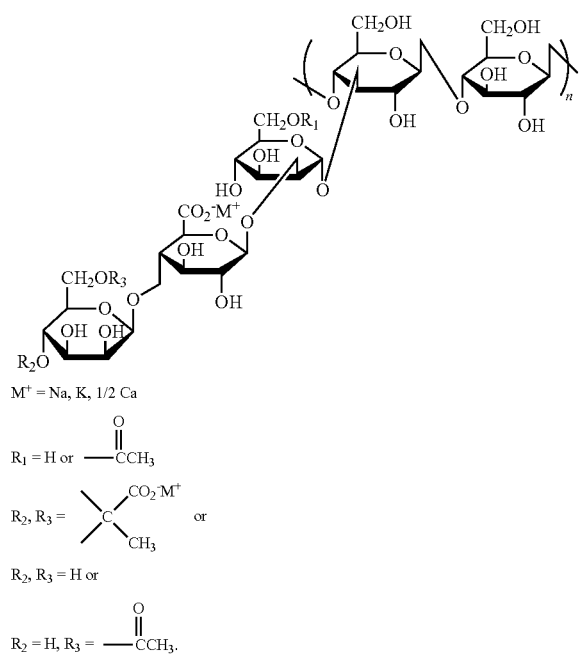

$M^+ = Na, K, 1/2\ Ca$ $R_1 = H$ or $-\overset{O}{\underset{\|}{C}}CH_3$ $R_2, R_3 = \overset{CO_2^-M^+}{\underset{CH_3}{>C<}}$ or $R_2, R_3 = H$ or $R_2 = H, R_3 = -\overset{O}{\underset{\|}{C}}CH_3$.

Xanthan by its structure constitutes a polyelectrolyte. The further special thickening agents cellulose gum (carboxymethyl cellulose) and hydroxyethyl cellulose are commercially available under the product names Cekol 5000 or Tylose H 100000 YP2. The hydroxyethylcellulose is a cellulose ether and substantially does not contain any free acid groups.

Preferred blonding agents contain at least one amino acid selected from arginine, lysine, histidine or at least one salt of these amino acids, in a total amount converted to the mass of free amino acid of from about 0.1-7% by weight, preferably from about 0.2-5% by weight, particularly preferably from about 0.5-2.5% by weight, most preferably from about 1-2% by weight, in each case based on the weight of blonding agent.

Blonding agents preferred as contemplated herein additionally contain at least one inorganic alkalizing agent which is solid at 20° C. and $10^5$ Pa, including at least one sodium silicate or sodium metasilicate having a molar $SiO_2/Na_2O$ ratio of ≥2, preferably from about 2.5 to about 3.5 in a total amount of from about 0.1 to about 50% by weight, preferably from about 5 to about 40% by weight, in each case based on the weight of blonding agent.

In addition to the at least one sodium silicate or sodium metasilicate having a molar $SiO_2/Na_2O$ ratio of ≥2, preferably from about 2.5-3.5, in a total amount of from about 0.1 to about 50% by weight, preferably from about 5 to about 40% by weight, in each case based on the weight of the blonding agent, inorganic alkalizing agents solid at 20° C. and $10^5$ Pa are selected from alkaline earth metal silicates, alkaline earth metal hydroxide carbonates, alkaline earth metal carbonates, alkaline earth metal metasilicates, alkali metal hydroxides, alkaline earth metal hydroxides, (earth) alkali metal phosphates and (earth) alkaline hydrogen phosphates, and mixtures of these substances are further particularly preferred as contemplated herein as an optional alkalizing agent. As contemplated herein particularly preferred inorganic alkalizing agents that are solid at 20° C. and $10^5$ Pa are, in addition to the at least one obligatory sodium silicate or sodium metasilicate, each having a molar $SiO_2/Na_2O$ ratio of ≥2, preferably from about 2.5 to about 3.5, selected from magnesium hydroxide carbonates and mixtures of these alkalizing agents. Magnesium hydroxide carbonates which are preferred as contemplated herein are those having the formula $MgCO_3 \cdot Mg(OH)_2 \cdot 2H_2O$ and those having the formula $MgCO_3 \cdot Mg(OH)_2$. Magnesium hydroxide carbonate having the formula $MgCO_3 \cdot Mg(OH)_2$ is particularly preferred as contemplated herein.

Blonding agents extremely preferred as contemplated herein contain, in each case based on their total weight, from about 10% to about 50% by weight, preferably from about 20% to about 40% by weight, of sodium silicates having a molar $SiO_2/Na_2O$ ratio of ≥2, preferably from about 2.5 to about 3.5, and from about 2-20% by weight, preferably from about 5-15% by weight, particularly preferably from about 10-13% by weight of magnesium hydroxide carbonate having the formula $MgCO_3 \cdot Mg(OH)_2$ as an inorganic alkalizing agent solid at 20° C. and $10^5$ Pa.

If the blonding agent as contemplated herein or preferred as contemplated herein contains one or more inorganic carbonates, be it as an alkalizing agent or as an oxidizing agent in the form of sodium carbonate-hydrogen peroxide complexes, its content is preferably selected such that in the application mixture, the molar $CO_3^2$ total concentration is at least about 0.015 mol/100 grams of application mixture.

If the blonding agent as contemplated herein or preferred as contemplated herein contains one or more inorganic carbonates, be it as an alkalizing agent or as an oxidizing agent in the form of sodium carbonate-hydrogen peroxide complexes, its content is particularly preferably selected such that in the application mixture, the molar $CO_3^2$ total concentration is mathematically at least four times higher than the total concentration of proton donors.

If the blonding agent as contemplated herein or preferred as contemplated herein contains one or more inorganic carbonates, be it as an alkalizing agent or as an oxidizing agent in the form of sodium carbonate-hydrogen peroxide complexes, its content is extremely preferably selected such that in the application mixture, the molar $CO_3^2$ total concentration is at least about 0.015 mol/100 grams of application mixture and is mathematically at least four times higher than the total concentrations of proton donors.

The blonding agent as contemplated herein preferably has a water content of from 0 to about 8% by weight, preferably from about 0.1 to about 5% by weight, particularly preferably from about 0.5 to about 3% by weight of water, in each case based on the weight of the blonding agent. The blonding agents can therefore be said to be substantially anhydrous.

This specification refers to the content of free water. Not taken into account is the content of molecularly bound water or water of crystallization which individual powder constituents can have. The water content can be determined, for example, based on ISO 4317 (version 2011-12) by employing Karl Fischer titration.

According to a further preferred embodiment, the blonding agent as contemplated herein contains at least one complexing agent selected from the acids mentioned below and/or their alkali metal salts: ethylenediaminetetraacetic acid (EDTA); N-hydroxyethylethylenediaminetriacetic acid; aminotrimethylenephosphonicacid; diethylenetriaminepentaacetic acid; lauroyl ethylenediamine triacetic acid; nitrilotriacetic acid; iminodisuccinic acid; N-2-hydroxyethyliminodiacetic acid; ethylene glycol-bis-(beta-aminoethyl ether)-N,N-tetraacetic acid; aminotrimethylenephosphonic acid, pentasodium aminotrimethylenephosphonate, and mixtures thereof, in a total amount of from about 0.1 to about 1.2% by weight, preferably from about 0.2 to about 1.3% by weight, particularly preferably from about 0.5 to about 1.4% by weight, in each case based on the weight of the blonding agent.

In a preferred embodiment, the blonding agent as contemplated herein further contains at least one dicarboxylic acid having from about 2 to about 10 carbon atoms or a tricarboxylic acid having from about 2 to about 10 carbon atoms, which is particularly preferably selected from succinic acid, malic acid, oxalic acid, malonic acid, adipic acid, pimelic acid, suberic acid, azelaic acid, sebacic acid, maleic acid, fumaric acid, D-tartaric acid, L-tartaric acid, meso-tartaric acid, racemic acid, alpha-ketoglutaric acid, beta-ketoglutaric acid, oxaloacetic acid, citric acid, and/or at least one salt of these acids and mixtures of these compounds, wherein the at least one dicarboxylic acid having from about 2 to about 10 carbon atoms is most preferably selected from succinic, malic and maleic acids and their salts.

Salts of the dicarboxylic acids having from about 2 to about 10 carbon atoms which are preferred as contemplated herein are selected from the mono- and disalts of the anions of succinic acid, malic acid, oxalic acid, malonic acid, adipic acid, pimelic acid, suberic acid, azelaic acid, sebacic acid, maleic acid, fumaric acid, D-tartaric acid, L-tartaric acid, meso-tartaric acid, racemic acid, alpha-ketoglutaric acid, beta-ketoglutaric acid and oxaloacetic acid with ammonium ions, alkali metal ions, alkaline earth metal ions and the ions of basic amino acids such as arginine, lysine and histidine, in particular with lithium, sodium, potassium, magnesium and calcium ions, and mixtures of these salts.

Particularly preferred succinic acid as contemplated herein has a melting point in the range from about 185-187° C. at $10^5$ Pa, that is, it is a solid at 20° C. Salts of succinic acid suitable as contemplated herein are selected from the succinates and hydrogen succinates of ammonium ions, alkali metal ions, alkaline earth metal ions and the ions of basic amino acids, such as arginine, lysine and histidine, in particular the lithium, sodium, potassium, magnesium and calcium ions, or the succinates and hydrogen succinates of basic amino acids, such as arginine, lysine and/or histidine, for example, arginine succinate, and mixtures of these salts. Said salts of succinic acid can also contain bound water of crystallization, in particular sodium succinate hexahydrate, which is particularly preferred as contemplated herein.

Particularly preferred malic acid as contemplated herein is optically active. Racemic DL-malic acid has a melting point in the range from about 131-132° C. at $10^5$ Pa, that is, it is a solid at 20° C. The enantiomers D-malic acid and L-malic acid each have a melting point in the range of from about 100-101° C. at $10^5$ Pa. Racemic DL-malic acid is preferred for cost reasons.

Salts of malic acid suitable as contemplated herein are selected from the malates and hydrogen malates of ammonium ions, alkali metal ions, alkaline earth metal ions and the ions of basic amino acids, such as arginine, lysine and histidine, in particular of lithium, sodium and potassium, magnesium and calcium ions, and mixtures of these salts, in particular disodium malate and dipotassium malate, but also calcium malate. Said salts of malic acid suitable as contemplated herein can contain bound water of crystallization, in particular disodium malate hemihydrate and disodium malate trihydrate.

Preferred oxalic acid as contemplated herein has a melting point of about 189.5° C. (anhydrous) at $10^5$ Pa or a melting point of about 101.5° C. as the dihydrate. Salts of oxalic acid suitable as contemplated herein are selected from the oxalates and hydrogen oxalates of ammonium ions, alkali metal ions, alkaline earth metal ions and the ions of basic amino acids, such as arginine, lysine and histidine, in particular of lithium, sodium, potassium, magnesium and calcium ions, and mixtures of these salts.

Preferred malonic acid as contemplated herein has a melting point of about 135° C. at $10^5$ Pa. Salts of malonic acid suitable as contemplated herein are selected from the malates and hydrogen malates of ammonium ions, alkali metal ions, alkaline earth metal ions and the ions of basic amino acids, such as arginine, lysine and histidine, in particular of lithium, sodium, potassium, magnesium and calcium ions, and mixtures of these salts.

Adipic acid preferred as contemplated herein has a melting point of about 152° C. at $10^5$ Pa. Salts of adipic acid which are suitable as contemplated herein are selected from the adipates and hydrogen adipates of ammonium ions, alkali metal ions, alkaline earth metal ions and the ions of basic amino acids, such as arginine, lysine and histidine, in particular of lithium, sodium, potassium, magnesium and calcium ions, and mixtures of these salts.

Preferred pimelic acid as contemplated herein has a melting point of about 105° C. at $10^5$ Pa. Pimelic acid salts which are suitable as contemplated herein are selected from the pimelates and hydrogen pimelates of ammonium ions, alkali metal ions, alkaline earth metal ions and the ions of basic amino acids, such as arginine, lysine and histidine, in particular lithium, sodium, potassium, magnesium and calcium ions, and mixtures of these salts.

Preferred suberic acid as contemplated herein has a melting point of about 144° C. at $10^5$ Pa. Salts of suberic acid suitable as contemplated herein are selected from the suberates and hydrogen suberates of ammonium ions, alkali metal ions, alkaline earth metal ions and the ions of basic amino acids, such as arginine, lysine and histidine, in particular of lithium, sodium, potassium, magnesium and calcium ions, and mixtures of these salts.

Preferred azelaic acid as contemplated herein has a melting point of about 106° C. at $10^5$ Pa. Salts of azelaic acid which are suitable as contemplated herein are selected from the azelates and hydrogen azelates of ammonium ions, alkali metal ions, alkaline earth metal ions and the ions of basic amino acids, such as arginine, lysine and histidine, in particular of lithium, sodium and potassium, magnesium and calcium ions, and mixtures of these salts.

Sebacic acid preferred as contemplated herein has a melting point of about 134.5° C. at $10^5$ Pa. Suitable salts of sebacic acid as contemplated herein are selected from the sebacates and hydrogen sebacates of ammonium ions, alkali metal ions, alkaline earth metal ions and the ions of basic amino acids, such as arginine, lysine and histidine, in particular of lithium, sodium and potassium, magnesium and calcium ions, and mixtures of these salts.

Maleic acid particularly preferred as contemplated herein has, at $10^5$ Pa, a melting point of about 130 to about 131° C. (from ethanol or benzene) and from about 138 to about 139° C. (from water). Salts of maleic acid suitable as contemplated herein are selected from the maleates and hydrogen maleates of ammonium ions, alkali metal ions and alkaline earth metal ions, in particular of lithium, sodium, potassium, magnesium and calcium ions, and mixtures of these salts.

Fumaric acid particularly preferred as contemplated herein has a melting point of about 287° C. in the sealed tube at $10^5$ Pa; at about 200° C., fumaric acid sublimes. Salts of fumaric acid suitable as contemplated herein are selected from the fumarates and hydrogen fumarates of ammonium ions, alkali metal ions and alkaline earth metal ions, in particular of lithium, sodium, potassium, magnesium and calcium ions, and mixtures of these salts.

Particularly preferred D-tartaric acid (levorotatory) as contemplated herein has a melting point of from about 168-170° C. at $10^5$ Pa. Salts of D-tartaric acid suitable as contemplated herein are selected from the tartrates and hydrogen tartrates of ammonium ions, alkali metal ions and alkaline earth metal ions, in particular of lithium, sodium, potassium, magnesium and calcium ions, and mixtures of these salts.

Particularly preferred L-tartaric acid (dextrorotatory) as contemplated herein has a melting point of from about 168-170° C. at $10^5$ Pa. Salts of L-tartaric acid suitable as contemplated herein are selected from the tartrates and hydrogen tartrates of ammonium ions, alkali metal ions and alkaline earth metal ions, in particular of lithium, sodium, potassium, magnesium and calcium ions, and mixtures of these salts.

Meso-tartaric acid particularly preferred as contemplated herein has a melting point of about 140° C. at $10^5$ Pa. Salts of meso-tartaric acid suitable as contemplated herein are selected from the tartrates and hydrogen tartrates of ammonium ions, alkali metal ions and alkaline earth metal ions, in particular of lithium, sodium, potassium, magnesium and calcium ions, and mixtures of these salts.

Particularly preferred racemic acid as contemplated herein is the racemic mixture of D-tartaric acid and L-tartaric acid. Racemic acid has a melting point of about 206° C. at $10^5$ Pa. Salts of racemic acid suitable as contemplated herein are selected from the tartrates and hydrogen tartrates of ammonium ions, alkali metal ions and alkaline earth metal ions, in particular of lithium, sodium, potassium, magnesium and calcium ions, and mixtures of these salts.

Particularly preferred alpha-ketoglutaric acid as contemplated herein has a melting point of from about 112-116° C. at $10^5$ Pa. Salts of alpha-ketoglutaric acid suitable as contemplated herein are selected from the alpha-ketoglutarates and alpha-ketohydrogen glutarates of ammonium ions, alkali metal ions and alkaline earth metal ions, in particular of lithium, sodium, potassium, magnesium and calcium ions, and mixtures of these salts.

Particularly preferred beta-ketoglutaric acid as contemplated herein has a melting point of about 122° C. at $10^5$ Pa; it melts with decomposition. Salts of beta-ketoglutaric acid suitable as contemplated herein are selected from the beta-ketoglutarates and beta-ketohydrogen glutarates of ammonium ions, alkali metal ions and alkaline earth metal ions, in particular of lithium, sodium, potassium, magnesium and calcium ions, and mixtures of these salts.

Particularly preferred oxaloacetic acid as contemplated herein has a melting point of about 161° C. at $10^5$ Pa. Salts of oxalacetic acid suitable as contemplated herein are selected from the oxalacetates and oxalhydrogen acetates of ammonium ions, alkali metal ions and alkaline earth metal ions, in particular of lithium, sodium, potassium, magnesium and calcium ions, and mixtures of these salts.

Salts of citric acid suitable as contemplated herein are selected from the citrates and hydrogen citrates of ammonium ions, alkali metal ions and alkaline earth metal ions, in particular of lithium, sodium, potassium, magnesium and calcium ions, and mixtures of these salts.

Blonding agents preferred as contemplated herein contain the at least one dicarboxylic acid having from about 2 to about 10 carbon atoms, selected from succinic acid, malic acid, oxalic acid, malonic acid, adipic acid, pimelic acid, suberic acid, azelaic acid, sebacic acid and/or at least one salt of these acids, in a total amount converted to the mass of free dicarboxylic acid of from about 0.03-7% by weight, preferably from about 0.1-5% by weight, particularly preferably from about 0.5-3% by weight, most preferably from about 0.9-1.5% by weight, in each case based on the weight of blonding agent.

Further blonding agents preferred as contemplated herein contain succinic acid and/or at least one salt of succinic acid in a total amount converted to the mass of free dicarboxylic acid of from about 0.03-7% by weight, preferably from about 0.1-5% by weight, particularly preferably from about 0.5-3% by weight, exceptionally preferably from about 0.9-1.5% by weight, in each case based on the weight of the blonding agent.

Further blonding agents preferred as contemplated herein contain malic acid and/or at least one salt of malic acid in a total amount converted to the mass of free dicarboxylic acid of from about 0.03-7% by weight, preferably from about 0.1-5% by weight, particularly preferably from about 0.5-3% by weight, exceptionally preferably from about 0.9-1.5% by weight, in each case based on the weight of the blonding agent.

For dedusting the blonding agent as contemplated herein, at least one dedusting agent can be added which is in particular selected from at least one oil, in particular selected from paraffin oil, silicone oil or ester oil and mixtures of these oils.

Blonding agents preferred as contemplated herein therefore additionally contain at least one oil in a total amount of from about 0.1-15% by weight, preferably from about 0.5-10% by weight, more preferably from about 1-8% by weight, most preferably from about 2-6% by weight, in each case based on the weight of blonding agent.

Oils preferred as contemplated herein are selected from natural and synthetic hydrocarbons, more preferably from paraffin oils, $C_{18}$-$C_{30}$ isoparaffins, in particular isoeicosane, polyisobutenes and polydecenes, furthermore selected from $C_8$-$C_{16}$ isoparaffins, in particular from isodecane, isododecane, isotetradecane and Isohexadecane and mixtures thereof, and 1,3-di-(2-ethylhexyl) cyclohexane.

Further preferred oils as contemplated herein are selected from the benzoic acid esters of linear or branched C8-22 alkanols. Particularly preferred are benzoic acid C12-C15 alkyl esters.

Further preferred oils are selected from fatty alcohols having from about 6-30 carbon atoms which are unsaturated or branched and saturated or branched and unsaturated. Preferred alcohol oils are 2-hexyldecanol, 2-octyldodecanol, 2-ethylhexyl alcohol and isostearyl alcohol.

Further preferred oils as contemplated herein are selected from the triglycerides (=triple esters of glycerol) of linear or branched, saturated or unsaturated, optionally hydroxylated C8-30 fatty acids. Particularly preferred can be the use of natural oils, for example, amaranth seed oil, apricot kernel oil, argan oil, avocado oil, babassu oil, cottonseed oil, borage seed oil, camelina oil, thistle oil, peanut oil, pomegranate seed oil, grapefruit seed oil, hemp oil, hazelnut oil, elderflower seed oil, currant seed oil, jojoba oil, linseed oil, macadamia nut oil, corn oil, almond oil, Marula oil, evening primrose oil, olive oil, palm oil, palm kernel oil, Brazil nut oil, pecan oil, peach kernel oil, rapeseed oil, castor oil, sea buckthorn fruit oil, sea buckthorn seed oil, sesame oil, soybean oil, sunflower oil, grapeseed oil, walnut oil, wild rose oil, wheat germ oil, and the liquid portions of coconut oil and the like. However, synthetic triglyceride oils are also preferred, in particular Capric/Caprylic Triglycerides.

Further preferred oils as contemplated herein are selected from the dicarboxylic acid esters of linear or branched $C_2$-$C_{10}$ alkanols, in particular diisopropyl adipate, di-n-butyl adipate, di-(2-ethylhexyl) adipate, dioctyl adipate, diethyl/di-n-butyl/dioctyl sebacate, diisopropyl sebacate, dioctyl malate, dioctyl maleate, dicaprylyl maleate, diisooctyl succinate, di-2-ethylhexyl succinate and di-(2-hexyldecyl) succinate.

Further particularly preferred cosmetic oils as contemplated herein are selected from the esters of linear or branched saturated or unsaturated fatty alcohols having from about 2-30 carbon atoms with linear or branched saturated or unsaturated fatty acids having from about 2 to about 30 carbon atoms which can be hydroxylated. These preferably include 2-hexyldecyl stearate, 2-hexyldecyl laurate, isodecyl neopentanoate, isononyl isononanoate, 2-ethylhexyl palmitate and 2-ethylhexyl stearate, isopropyl myristate, isopropyl palmitate, isopropyl stearate, isopropyl isostearate, isopropyl oleate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyl dodecyl palmitate, butyloctanoic acid 2-butyl octanoate, diisotridecyl acetate, n-butyl stearate, n-hexyl laurate, n-decyl oleate, oleyl oleate, oleyl erucate, erucyl oleate, erucyl erucate, ethylene glycol dioleate and ethylene glycol dipalmitate.

Further preferred cosmetic oils as contemplated herein are selected from the addition products of 1 to 5 propylene oxide units of mono- or multivalent $C_8$-$C_{22}$ alkanols such as octanol, decanol, decanediol, lauryl alcohol, myristyl alcohol and stearyl alcohol, for example, PPG-2 myristyl ether and PPG-3 myristyl ether. Further preferred cosmetic oils as contemplated herein are selected from the addition products of at least 6 ethylene oxide and/or propylene oxide units of monovalent or polyvalent $C_{3-22}$ alkanols such as glycerol, butanol, butanediol, myristyl alcohol and stearyl alcohol, which can be esterified if desired, for example, PPG-14 butyl ether, PPG-9-butyl ether, PPG-10-butanediol, PPG-15 stearyl ether and glycereth-7-diisononanoate.

Further preferred cosmetic oils as contemplated herein are selected from the $C_8$-$C_{22}$ fatty alcohol esters of monovalent or multivalent $C_2$-$C_7$ hydroxycarboxylic acids, in particular the esters of glycolic acid, lactic acid, malic acid, tartaric acid, citric acid and salicylic acid, for example, $C_{12}$-$C_{15}$ alkyl lactate.

Further preferred cosmetic oils as contemplated herein are selected from the symmetrical, asymmetric or cyclic esters of carbonic acid with $C_{3-22}$ alkanols, $C_{3-22}$ alkanediols or $C_{3-22}$ alkanetriols, for example, dicaprylyl carbonate, or the esters according to DE 19756454 A1, in particular glycerol carbonate.

Further cosmetic oils as contemplated herein which are suitable are selected from silicone oils including, for example, dialkyl and alkylaryl siloxanes such as decamethylcyclopentasiloxane, dodecamethylcyclohexasiloxane, dimethylpolysiloxane and methylphenylpolysiloxane, but also hexamethyldisiloxane, octamethyltrisiloxane and decamethyltetrasiloxane.

It can be extremely preferable as contemplated herein to use mixtures of the aforementioned oils.

Preferred blonding agents as contemplated herein include cosmetic oil that is selected from natural and synthetic hydrocarbons, more preferably from paraffin oils, $C_{18}$-$C_{30}$ isoparaffins, in particular isoeicosane, polyisobutenes and polydecenes, $C_8$-$C_{16}$ isoparaffins, and 1,3-di-(2-ethylhexyl) cyclohexane; the benzoic acid esters of linear or branched $C_{8-22}$ alkanols; fatty alcohols having from about 6-30 carbon atoms which are unsaturated or branched and saturated or branched and unsaturated; triglycerides of linear or branched, saturated or unsaturated, optionally hydroxylated $C_{8-30}$ fatty acids, in particular natural oils; the dicarboxylic acid esters of linear or branched $C_2$-$C_{10}$ alkanols; the esters of linear or branched saturated or unsaturated fatty alcohols having from about 2-30 carbon atoms with linear or branched saturated or unsaturated fatty acids having from about 2-30 carbon atoms which can be hydroxylated; the addition products of 1 to 5 propylene oxide units of monovalent or polyvalent $C_{8-22}$ alkanols; the addition products of at least 6 ethylene oxide and/or propylene oxide units of monovalent or polyvalent $C_{3-22}$ alkanols; $C_8$-$C_{22}$ fatty alcohol esters of monovalent or polyvalent $C_2$-$C_7$ hydroxycarboxylic acids; the symmetrical, asymmetrical or cyclic esters of carbonic acid with $C_{3-22}$ alkanols, $C_{3-22}$ alkanediols or $C_{3-22}$ alkanetriols; the esters of dimers of unsaturated $C_{12}$-$C_{22}$ fatty acids (dimer fatty acids) with monovalent linear, branched or cyclic $C_2$-$C_{18}$ alkanols or with polyvalent linear or branched $C_2$-$C_6$ alkanols; silicone oils and mixtures of the aforementioned substances and preferably is present in a total amount of from about 0.1-15% by weight, preferably from about 0.5-10% by weight, particularly preferably from about 1-8% by weight, most preferably from about 2-6% by weight, in each case based on the weight of blonding agent.

Further preferred blonding agents as contemplated herein contain at least one polymer selected from acrylic acid homopolymers and copolymers, methacrylic acid homopolymers and copolymers, itaconic acid homopolymers and copolymers, polysaccharides, which can be chemically and/or physically modified, and mixtures of these polymers, wherein particularly preferably one or more of said polymers is present in a total amount of from about 0.1-6% by weight, preferably from about 0.5-4% by weight, particularly preferably from about 1-3.5% by weight, most preferably from about 2-3% by weight, in each case based on the weight of blonding agent.

Further preferred ingredients of the blonding agent are listed in the following: sodium chloride in an amount of from about 0.1-5% by weight, preferably from about 0.2-3% by weight, particularly preferably from about 0.3-1% by weight, most preferably from about 0.5-0.7% by weight, in each case based on the weight of the blonding agent.

Dicarboxylic acids having from about 2 to 10 carbon atoms which are preferably selected from succinic acid, malic acid, oxalic acid, malonic acid, adipic acid, pimelic acid, suberic acid, azelaic acid, sebacic acid, maleic acid, fumaric acid, D-tartaric acid, L-tartaric acid, meso-tartaric acid, racemic acid, alpha-ketoglutaric acid, beta-ketoglutaric acid, oxaloacetic acid, and/or at least one salt of these acids, particularly preferably in a total amount converted to the mass of free dicarboxylic acid of from about 0.03-7% by weight, preferably from about 0.1-5% by weight, particularly preferably from about 0.5-3% by weight, most preferably from about 0.9-1.5% by weight, in each case based on the weight of blonding agent.

Amino acids selected from arginine, lysine, histidine or at least one salt of these amino acids, in a total amount converted to the mass of free amino acid of from about 0.1-7% by weight, preferably from about 0.2 to about 5% by weight, more preferably from about 0.5-2.5% by weight, most preferably from about 1-2% by weight, in each case based on the weight of the blonding agent.

In addition to blonding, consumers, in particular female consumers, desire a slight color shift, known in the art as shading, together with a color lightening. The use of solid oxidizing agents with dyes poses a problem to the developers of cosmetic agents which cause a blonding and shading effect. The oxidizing agents, in particular the persulfates, react with dye precursors, so that they lose their effect or that they cause a difficult to control color shift.

The object underlying the present disclosure is also to provide a cosmetic product that has easy handling and shows a blonding and a shading effect.

The object underlying the present disclosure is solved by the blonding agents as contemplated herein. A second subject of the present disclosure is therefore a cosmetic product comprising a blonding agent as contemplated herein and a packaging, wherein the blonding agent is contained in the packaging and the packaging includes a multilayer film (F), wherein the film (F) has a barrier layer (BS) which is impermeable to water vapor. The impermeability of water vapor is caused by the barrier layer of the film. The impermeability is to be provided when the water vapor transmission rate, as defined in more detail below, is less than about $0.1\ g/(m^2 24\ h)$. This is preferably ensured when the barrier layer (BS) comprises a metal, in particular aluminum, or $SiO_x$. That is, according to a preferred embodiment of this subject as contemplated herein, the barrier layer comprises a metal, in particular aluminum, or $SiO_x$. Alternatively, the barrier layer can also constitute another ceramic layer, for example, $AlO_x$. In a further alternative, instead of the multilayer film comprising the layer impermeable to water vapor, it would also be possible to use a glass bottle which contains the blonding agent as contemplated herein.

The object underlying the present disclosure is achieved since the penetration of moisture into the packaging is prevented. This prevents oxidation agents and oxidation dyes from be able to react with each other. Small amounts of oxidation dye precursors can therefore be included in the cosmetic product. At the same time, the advantageous effect with respect to viscosity is achieved by the cosmetic product containing the three thickening agents according to the first subject of the present disclosure.

According to a preferred embodiment of the present disclosure, the cosmetic product comprises a blonding agent and a packaging, wherein the blonding agent is contained in the packaging and the packaging includes a multilayer film (F), wherein the film (F) has a barrier layer (BS), which comprises a metal, in particular aluminum, or $SiO_x$, wherein the blonding agent for changing the natural color of keratinic fibers, in particular human hair, comprises a cosmetic composition (KM), wherein the cosmetic composition (KM) contains at least one solid oxidizing compound and
a mixture of thickening agents,
wherein the mixture of thickening agents comprises a cellulose gum, a hydroxyethyl cellulose and a xanthan gum.

According to a preferred embodiment of the present disclosure, the cosmetic product comprises a blonding agent and a packaging, wherein the blonding agent is contained in the packaging and the packaging includes a multilayer film (F), wherein the film (F) has a barrier layer (BS), which comprises a metal, in particular aluminum, or $SiO_x$, wherein the blonding agent for changing the natural color of keratinic fibers, in particular human hair, comprises a cosmetic composition (KM), wherein the cosmetic composition (KM) contains at least one solid oxidizing compound,
at least one direct acting dye and
a mixture of thickening agents,
wherein the mixture of thickening agents comprises a cellulose gum, a hydroxyethyl cellulose and a xanthan gum.

The blonding agents can be contained in packagings of preferred film materials. The film materials are of particular importance in the storage of a multicomponent system, since substances from the multicomponent system can diffuse into the films and can promote a detachment of layers which form the film.

According to a preferred embodiment of the present disclosure, the multilayer film (F) comprises at least a first polymer layer (P1), at least a second polymer layer (P2) and the barrier layer (BS), wherein the first polymer layer (P1) is formed of polyethylene terephthalate or polyethylene naphthalate, in particular polyethylene terephthalate; and the second polymer layer (P2) is formed of a polyolefin, in particular polyethylene. Furthermore, it is preferred that the first polymer layer (P1) has a layer thickness of from about 5 to about 20 μm, preferably from about 8 to about 16, more preferably from about 10 to about 14 μm, and the second polymer layer has a layer thickness of from about 50 to about 100 μm, preferably from about 60 to about 90 μm, more preferably from about 70 to about 80 μm.

According to a preferred embodiment, the barrier layer (BS) is arranged between the first polymer layer (P1) and the second polymer layer (P2). Particularly preferably, the first polymer layer is located on the side facing away from the cosmetic composition side. It is to be understood that the second polymer layer is internal and the first polymer layer is external. This arrangement is particularly advantageous in the solution of the object underlying the present disclosure. The barrier layer comprises a metal, in particular aluminum, or $SiO_x$.

As contemplated herein, the permeability values of the film (F) are advantageously adjusted. The film (F) thus gives the packaging advantageous barrier properties, in particular with regard to the permeability to water vapor (Water Vapor Transmission Rate; WVTR; measured in units of $g/(m^2 d)$ or $g/(m^2 24\ h)$) measured by the method ASTM F 1249 at 38° C. ambient temperature and 100% relative humidity, and for oxygen (Oxygen Transmission Rate; OTR, measured in $cm^3/(m^2 d\ bar)$ or $cm^3/(m^2 24\ h)$—wherein $cm^3$ is equivalent to cc—at an atmospheric pressure of 1 bar) measured by the method ASTM D 3985 at 23° C. ambient temperature and 50% relative humidity. The multilayer film (F) of the packaging of the cosmetic product as contemplated herein is distinguished by advantageous properties with regard to oxygen transmission rate and water vapor transmission rate. The multilayer film exhibits an oxygen transmission rate (OTR) at 23° C. and 50% relative humidity of less than about 0.1, and in particular a water vapor transmission rate at 38° C. and 100% relative humidity of less than about 0.1. The choice of the material of the film (F) and the layer thicknesses of the components are of particular importance for the solution of the object underlying the present disclosure, since the object can be solved exceptionally well.

Furthermore, the blonding agents as contemplated herein or preferred as contemplated herein and thus the cosmetic products as contemplated herein can contain at least one direct acting dye. These are dyes that are applied directly to the hair and do not require an oxidative process to form the color. For matting unwanted residual color impressions caused by melanin degradation products, in particular in the reddish or bluish range, particular direct acting dyes of the complementary colors are particularly preferred. Direct dyes are usually nitrophenylenediamines, nitroaminophenols, azo dyes, anthraquinones or indophenols. Direct dyes can be anionic, cationic or nonionic. The direct acting dyes are each preferably present in an amount of from about 0.001 to about 2% by weight, based on the weight of the blonding agent.

Preferred anionic direct acting dyes are those compounds known under the international designations or trade names Acid Yellow 1, Yellow 10, Acid Yellow 23, Acid Yellow 36, Acid Orange 7, Acid Red 33, Acid Red 52, Pigment Red 57, Acid Blue 7, Acid Green 50, Acid Violet 43, Acid Black 1, Acid Black 52, bromophenol blue and tetrabromophenol blue. Preferred cationic direct acting dyes are cationic triphenylmethane dyes such as Basic Blue 7, Basic Blue 26, Basic Violet 2 and Basic Violet 14, aromatic systems which are substituted with a quaternary nitrogen group such as Basic Yellow 57, Basic Red 76, Basic Blue 99, Basic Brown 16 and Basic Brown 17, cationic anthraquinone dyes such as HC Blue 16 (Bluequat B) and direct acting dyes which contain a heterocycle having at least one quaternary nitrogen atom, in particular Basic Yellow 87, Basic Orange 31 and Basic Red 51. The cationic direct acting dyes that are sold under the trademark Arianor are also preferred cationic direct acting dyes as contemplated herein. In particular, nonionic nitro and quinone dyes and neutral azo dyes are suitable nonionic direct acting dyes. Preferred nonionic direct acting dyes are those compounds known under the international names or trade names Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, and 1,4-diamino-2-nitrobenzene, 2-amino-4-nitrophenol, 1,4-bis-(2-hydroxyethyl)-amino-2-nitrobenzene, 3-nitro-4-(2-hydroxyethyl) aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-4-nitrophenol. Very particularly preferred as contemplated herein is a combination of tetrabromophenol blue and Acid Red 92.

At least one oxidation dye precursor is preferably used as a further optional ingredient, which oxidation dye precursor is preferably selected from one or more developer components and optionally one or more coupler components.

Particularly preferably, at least one oxidation dye precursor is present in a total amount of from about 0.0001 to about 10.0% by weight, preferably from about 0.001 to about 8% by weight, in each case based on the weight of the blonding agent.

It can be preferred as contemplated herein to select as the developer component at least one compound from the group which is formed from p-phenylenediamine, p-toluenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diamino-propan-2-ol, bis-(2-hydroxy-5-aminophenyl) methane, 1,3-bis-(2,5-diaminophenoxy)propan-2-ol, N,N-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl) phenol, 4-amino-2-(diethylaminomethyl) phenol, 4,5-diamino-1-(2-hydroxyethyl) pyrazole, 2,4,5,6-tetraaminopyrimidine, 4-hydroxy-2,5,6-triaminopyrimidine, 2-hydroxy-4,5,6-triaminopyrimidine, and their physiologically compatible salts.

Preferably, at least one developer component is present in a total amount of from about 0.0001 to about 10.0% by weight, preferably from about 0.001 to about 8% by weight, in each case based on the weight of the blonding agent.

Coupler components do not alone form significant dyeing in the context of oxidative dyeing, but always require the presence of developer components. Therefore, it is preferred as contemplated herein that at least one coupler component is additionally used when using at least one developer component.

Preferred coupler components as contemplated herein are selected from 3-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2-hydroxyethyl) amino-2-methylphenol, 3-(diethylamino) phenol, N-cyclopentyl-3-aminophenol, 1,3-dihydroxy-5-(methylamino) benzene, 3-ethylamino-4-methylphenol, 2,4-dichloro-3-aminophenol, 2-(2,4-diaminophenoxy) ethanol, 1,3-bis (2,4-diaminophenoxy) propane, 1-methoxy-2-amino-4-(2-hydroxyethylamino) benzene, 1,3-bis-(2,4-diaminophenoxy) propane, 2,6-bis-(2'-hydroxyethylamino)-1-methylbenzene, 2-({3-[(2-hydroxyethyl) amino]-4-methoxy-5-methylphenyl}amino) ethanol, 2-({3-[(2-hydroxyethyl) amino]-2-methoxy-5-methylphenyl}amino) ethanol, 2-({3-[(2-hydroxyethyl) amino]-4,5-dimethylphenyl}amino) ethanol, 2-[3-morpholine-4-ylphenyl) amino]ethanol, 3-amino-4-(2-methoxyethoxy)-5-methylphenylamine, 1-amino-3-bis-(2-hydroxyethyl) aminobenzene, resorcinol, resorcinol monomethyl ether, 2-methylresorcinol, 5-methylresorcinol, 2,5-dimethylresorcinol, 2-chlororesorcinol, 4-chlororesorcinol, pyrogallol, 1,2,4-trihydroxybenzene, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 2,6-dihydroxy-3,4-dimethylpyridine, 3,4-diaminopyridine, 2-(2-methoxy ethyl) amino-3-amino-6-methoxypyridine, 2-(4'-methoxyphenyl) amino-3-aminopyridine, 1-naphthol, 2-methyl-1-naphthol, 2-hydroxymethyl-1-naphthol, 2-hydroxy ethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene, 2,3-dihydroxynaphthalene, 4-hydroxyindole, 6-hydroxyindole, 7-hydroxyindole, 4-hydroxyindoline, 6-hydroxyindoline, 7-hydroxyindoline, 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine or mixtures of these compounds or their physiologically compatible salts.

Preferably, at least one coupler component is present in a total amount of from about 0.0001 to about 10.0% by weight, preferably from about 0.001 to about 8% by weight, in each case based on the weight of the blonding agent.

In this case, developer components and coupler components are generally used in approximately equimolar amounts to each other. Although the equimolar use has proved to be expedient, a certain excess of individual oxidation dye precursors is not disadvantageous, so that developer components and coupler components can be present in a molar ratio of from about 0.2-2, in particular from about 0.5-1.

Since, in the treatment of keratinic fibers, in particular hair, with oxidizing agents, the fibrous dye melanin is destroyed to some degree, the fibers/hair are inevitably lightened, thus changing their color, with and without the presence of a dye. Therefore, the term "color change" in the context of the present application encompasses both lightening and staining with one or more dyes.

Furthermore, cosmetic agents preferred as contemplated herein contain at least one surfactant or at least one emulsifier, preferably in a total amount of from about 0.5-10% by weight, preferably from about 1-5% by weight, in each case based on the weight of the blonding agent used as contemplated herein.

Surfactants and emulsifiers in the context of the present application are amphiphilic (bifunctional) compounds which include at least one hydrophobic and at least one hydrophilic molecule part. The hydrophobic radical is preferably a hydrocarbon chain having from about 8-28 carbon atoms, which can be saturated or unsaturated, linear or branched. Particularly preferably, this $C_8$-$C_{28}$ alkyl chain is linear. Basic properties of the surfactants and emulsifiers are the oriented absorption at interfaces and the aggregation to micelles and the formation of lyotropic phases.

Anionic, nonionic and cationic surfactants are particularly suitable as contemplated herein. However, zwitterionic and amphoteric surfactants are also very suitable as contemplated herein.

All anionic surfactants suitable for use on the human body are suitable as anionic surfactants in the compositions as contemplated herein. These are exemplified by a water-solubilizing, anionic group such as a carboxylate, sulfate, sulfonate or phosphate group and a lipophilic alkyl group having from about 8 to about 30 carbon atoms. In addition, glycol or polyglycol ether groups, ester, ether and amide groups and hydroxyl groups can be present in the molecule. Examples of suitable anionic surfactants are linear and branched fatty acids having from about 8 to about 30 carbon atoms (soaps), alkyl ether carboxylic acids, acylsarcosides, acyl taurides, acyl isethionates, sulfosuccinic acid mono and dialkyl esters, sulfosuccinic acid monoalkyl polyoxyethyl esters, linear alkanesulfonates, linear alpha-olefinsulfonates, alkyl sulfates and alkyl ether sulfates and alkyl and/or alkenyl phosphates. Preferred anionic surfactants are alkyl sulfates, alkyl ether sulfates and alkyl ether carboxylic acids having in each case from about 10 to about 18 C atoms, preferably from 12 to 14 C atoms in the alkyl group and up to 12 glycol ether groups, preferably 2 to 6 glycol ether groups in the molecule. Examples of such surfactants are the compounds with the INCI names Sodium Laureth Sulfate, Sodium Lauryl Sulfate, Sodium Myreth Sulfate or Sodium Laureth Carboxylate.

Zwitterionic surfactants are surface-active compounds which carry at least one quaternary ammonium group and at least one carboxylate, sulfonate or sulfate group in the molecule. Particularly suitable zwitterionic surfactants are the so-called betaines such as N-alkyl-N,N-dimethylammonium glycinates, for example, cocoalkyl dimethylammonium glycinate, N-acylaminopropyl N,N-dimethylammonium glycinates, for example, cocoacylaminopropyl-dimethylammonium glycinate, and 2-alkyl-3-carboxymethyl-3-hydroxyethyl-imidazolines each having from about 8 to about 18 carbon atoms in the alkyl or acyl group and cocoacylamino ethyl hydroxyethyl carboxymethyl glycine. A preferred zwitterionic surfactant is the fatty acid amide derivative known by the INCI name Cocamidopropyl Betaine.

Amphoteric surfactants are understood to mean those surface-active compounds which, apart from a $C_8$-$C_{24}$ alkyl or acyl group in the molecule, contain at least one free amino group and at least one —COOH or —SO$_3$H group and which are capable of forming internal salts. Examples of suitable amphoteric surfactants are N-alkylglycines, N-alkylpropionic acids, N-alkylaminobutyric acids, N-alkyliminodipropionic acids, N-hydroxy ethyl-N-alkylamidopropylglycine, N-alkyltaurines, N-alkylsarcosines, 2-alkylaminopropionic acids and alkylaminoacetic acids, each having from about 8 to about 24 carbon atoms in the alkyl group. Particularly preferred amphoteric surfactants are N-coco alkylamine propionate and $C_{12}$-$C_{18}$ acylsarcosine.

Nonionic surfactants contain as hydrophilic group, for example, a polyol group, a polyalkylene glycol ether group or a combination of polyol and polyglycol ether groups. Such compounds are, for example, addition products of from about 4 to about 50 moles of ethylene oxide and/or from 0 to 5 moles of propylene oxide with linear and branched fatty alcohols, on fatty acids and on alkylphenols, each having from about 8 to about 20 carbon atoms in the alkyl group, ethoxylated mono-, di- and triglycerides, such as glycerol monolaurate+20 ethylene oxide, and glycerol monostearate+20 ethylene oxide, sorbitan fatty acid esters and addition products of ethylene oxide on sorbitan fatty acid esters such as the polysorbates (Tween 20, Tween 21, Tween 60, Tween 61, Tween 81), addition products of ethylene oxide on fatty acid alkanolamides and fatty amines, and alkylpolyglycosides. Suitable nonionic surfactants are, in particular, $C_8$-$C_{22}$ alkyl mono- and -oligoglycosides and their ethoxylated analogs and ethylene oxide addition products on saturated or unsaturated linear fatty alcohols with from about 2 to about 30 mole of ethylene oxide per mole of fatty alcohol.

Further blonding agents preferably used as contemplated herein include at least one anionic surfactant that is selected from alkyl sulfates, alkyl ether sulfates and alkyl ether carboxylic acids, each having from about 10 to about 18 C atoms, preferably 12 to 14 C atoms in the alkyl group and up to 12, preferably 2 to 6 glycol ether groups, in the molecule.

Further blonding agents preferably used as contemplated herein are exemplified in that at least one nonionic surfactant selected from ethylene oxide addition products of saturated or unsaturated linear fatty alcohols each with from about 2 to about 30 moles of ethylene oxide per mole of fatty alcohol, and at least one anionic surfactant selected from alkyl sulfates, alkyl ether sulfates and alkyl ether carboxylic acids each having from about 10 to about 18 C atoms, preferably 12 to 14 C atoms in the alkyl group and up to 12, preferably from about 2 to about 6 glycol ether groups, is present in the molecule, wherein particularly preferred the weight ratio of the total of all anionic surfactants to the total of all nonionic surfactants is in the range of from about 5-50, preferably from about 10-30.

Suitable cationic surfactants in blonding agents preferably used as contemplated herein are in principle all cationic surface-active substances suitable for use on the human body. These are exemplified by at least one water-solubilizing, cationic group, such as a quaternary ammonium group, or by at least one water-solubilizing, cationizable group such as an amine group, and further at least one (lipophilic-acting) alkyl group having from about 6 to about 30 carbon atoms or at least one (lipophilic-acting) imidazole group or at least one (lipophilic-acting) imidazylalkyl group.

Blonding agents used particularly preferably as contemplated herein contain at least one cationic surfactant, which is preferably selected from quaternary ammonium compounds having at least one C8-C24 alkyl radical, esterquats and amidoamines each having at least one C8-C24 acyl radical and mixtures thereof. Preferred quaternary ammonium compounds having at least one C8-C24 alkyl radical are ammonium halides, in particular chlorides, and ammonium alkyl sulfates, such as methosulfates or ethosulfates, such as C8-C24 alkyltrimethylammonium chlorides, C8-C24 dialkyldimethylammonium chlorides and C8-C24 trialkylmethylammonium chlorides, for example, cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, and the imidazolium compounds known under the INCI names Quaternium-27, Quaternium-83, Quaternium-87 and Quaternium-91. The alkyl chains of the above-mentioned surfactants preferably have from about 8 to about 24 carbon atoms.

Esterquats are cationic surfactants which contain both at least one ester function and at least one quaternary ammonium group as a structural element and furthermore at least one C8-C24 alkyl radical or C8-C24 acyl radical. Preferred esterquats are quaternized ester salts of fatty acids with triethanolamine, quaternized ester salts of fatty acids with diethanolalkylamines and quaternized ester salts of fatty acids with 1,2-dihydroxypropyldialkylamines. Such products are sold, for example, under the trademarks Stepantex®, Dehyquart® and Armocare®. N,N-bis(2-palmitoyloxyethyl) dimethylammonium chloride, distearoylethyl dimonium methosulfate and distearoylethyl hydroxyethylmonium methosulfate are preferred examples of such ester quats.

The alkylamidoamines are usually prepared by amidation of natural or synthetic C8-C 24 fatty acids and fatty acid cuts prepared with di (C1-C3) alkylaminoamines. A particularly suitable compound of this substance group as contemplated herein is stearamidopropyldimethylamine.

Blonding agents used particularly preferably as contemplated herein contain at least one cationic surfactant in a total amount of from about 0.01-5% by weight, preferably from about 0.1-3% by weight, particularly preferably from about 0.3-2% by weight, in each case based on the weight of the blonding agent used as contemplated herein.

A further object of the present disclosure was to provide a method with which keratinic fibers, in particular human hair, can be blonded and/or shaded, the method being easy to handle. The object underlying the present disclosure is solved by the methods of for lightening keratinic fibers as contemplated herein. A further subject of the present disclosure is therefore a method for lightening keratinic fibers, in particular human hair, in which the blonding agent as contemplated herein is mixed with water, the resulting mixture is applied immediately after mixing on the keratin-containing fibers and, is left on the keratinic fibers from about 5 to about 60 minutes, the keratin-containing fibers are then rinsed with water and/or rinsed with water and a surfactant-containing cleaning agent.

The method allows blonding using a cosmetic composition that only needs to be mixed with water. The use of a hydrogen peroxide solution is eliminated since the percarbonate, when mixed with water, creates a substance that has the same effect as hydrogen peroxide. The powder, which constitutes the blonding agent, can be packed in a space-saving manner. The ease of handling is achieved by the methods as contemplated herein. Furthermore, the method allows advantageous ease of handling in that the three thickening agents are contained in the blonding agent, so that the viscosity advantageously develops over time, as described above.

As contemplated herein, the blonding agent is preferably composed such that the mixture of the components essential to the present disclosure for the production of the ready-to-use blonding agent has an alkaline pH value, preferably a pH value of from about 8 to about 11.5, particularly preferably a pH value of from about 8.5 to about 11, most preferably a pH value of from about 9.0 to about 10.5, each measured at 20° C.

According to a preferred embodiment of the present disclosure, there is provided a method in which the blonding agent is mixed with water in a weight ratio of blonding agent to water of from about 1 to about 1 to about 1 to about 4, preferably from about 1 to about 2 to about 1 to about 3.

The ready-to-use mixtures of a blonding agent as contemplated herein or preferred as contemplated herein with water preferably have a viscosity in the range from about 15,000 to about 100,000 mPas, particularly preferably from about 20,000 to about 85,000 mPas, respectively measured at 20° C. with a Brookfield viscometer type DV-II+, spindle 5 at a speed of 4 revolutions/minute. A viscosity in this range allows the ready-to-use cosmetic agent to be well applied on the one hand and have a flow behavior on the other hand to ensure that the agent has a sufficiently long exposure time on the keratinic fibers at the site of action.

The exposure time is preferably from about 5 to about 60 minutes, in particular from about 7 to about 50 minutes, particularly preferably from about 10 to about 45 minutes. During the exposure time of the agents on the fiber, it can be advantageous to assist the lightening or color changing process by supplying heat. An exposure phase at room temperature is also as contemplated herein. In particular, the temperature during the exposure time lies between about 20° C. and about 40° C., in particular between about 25° C. and about 38° C. The agents yield good treatment results even at physiologically compatible temperatures of below about 45° C.

After the end of the color-changing operation, all components located on the keratinic fibers are rinsed out of the hair with water and/or with water and a surfactant-containing cleaning agent. Commercial shampoo in particular can be used as a cleaning agent in this case, wherein in particular the cleaning agent can then be dispensed with and the rinsing process can be done with tap water when the color-changing agent or the blonding agent has surfactants or a high content of surfactant.

The following objects are to be disclosed in further alternative embodiments:

Blonding agent for changing the natural color of keratinic fibers, in particular human hair, comprising a cosmetic composition (KM), wherein the cosmetic composition (KM) contains
    at least one oxidizing compound,
    at least one percarbonate, and
    at least one thickening agent,
exemplified in that the at least one oxidizing compound is an inorganic salt of a peroxosulfuric acid and the at least one thickening agent is present in the blonding agent in an amount of from about 3 to about 15% by weight, preferably from about 4 to about 13% by weight, more preferably from about 5 to about 11% by weight, most preferably from about 6 to about 9% by weight, based on the total weight of the blonding agent.

Blonding agent as contemplated herein, may include inorganic salt of a peroxosulfuric acid that is selected from the group of sodium peroxodisulfate, potassium peroxodisulfate, ammonium peroxodisulfate, sodium peroxomonosulfate, potassium peroxomonosulfate and ammonium peroxomonosulfate, or mixtures of these inorganic salts of a peroxosulfuric acid, preferably mixtures of potassium peroxodisulfate and ammonium peroxodisulfate or mixtures of sodium peroxodisulfate and ammonium peroxodisulfate, wherein preferably the total amount of inorganic salt of a peroxosulfuric acid is from about 10 to about 70% by weight, more preferably from about 20 to about 50% by weight, even more preferably from about 25 to about 45% by weight, most preferably from about 30 to about 40% by weight, in each case based on the total weight of the blonding agent.

Blonding agent as contemplated herein, may include inorganic salt of a peroxosulfuric acid that constitutes a mixture comprising 5 to 40% by weight, preferably from about 10 to about 35% by weight, more preferably from about 15 to about 30% by weight of potassium peroxodisulfate, from about 5 to about 20% by weight, preferably from about 8 to about 18% by weight, more preferably from about 10 to about 15% by weight of ammonium peroxodisulfate and from 0 to about 10% by weight, preferably from about 1 to about 9% by weight, more preferably from about 2 to about 6% by weight of sodium perooxodisulfate, in each case based on the total weight of the blonding agent.

Blonding agent as contemplated herein, may further include at least one inorganic alkalizing agent that is solid at 20° C. and $10^5$ Pa is present, including at least one sodium silicate or sodium metasilicate having a molar $SiO_2/Na_2O$ ratio of ≥2, preferably from about 2.5 to about 3.5, in a total amount of from about 10 to about 50% by weight, preferably from about 20 to about 40% by weight, in each case based on the weight of the blonding agent.

Blonding agent as contemplated herein, may further include at least one complexing agent selected from the acids mentioned below and/or their alkali metal salts is present: ethylenediaminetetraacetic acid (EDTA); N-hydroxyethylethylenediaminetriacetic acid; aminotrimethylenephosphonicacid; diethylenetriaminepentaacetic acid; lauroyl ethylenediamine triacetic acid; nitrilotriacetic acid; iminodisuccinic acid; N-2-hydroxyethyliminodiacetic acid; ethylene glycol-bis-(beta-aminoethyl ether)-N,N-tetraacetic acid; aminotrimethylenephosphonic acid, pentasodium aminotrimethylenephosphonate, and mixtures thereof, in a total amount of from about 0.1 to about 1.4% by weight, preferably from about 0.2 to about 1.4% by weight, particularly preferably from about 0.5 to about 1.4% by weight, in each case based on the weight of the blonding agent.

Blonding agent as contemplated herein, may include at least one percarbonate that constitutes an alkali metal, alkaline earth metal or ammonium salt of a percarbonate, in particular sodium percarbonate, and/or may include at least one percarbonate, in particular sodium percarbonate, that is present in the blonding agent in a total amount of from about 2 to about 14% by weight, preferably from about 4 to about 12% by weight, more preferably from about 6 to about 10% by weight, based on the total weight of the blonding agent.

Cosmetic agent as contemplated herein, may further include at least one thickening agent that is a polysaccharide, preferably a mixture of at least two different polysaccharides, more preferably a mixture of an at least partially ionic polysaccharide and a substantially non-ionic polysaccharide, and/or may include at least one thickening agent that is present in the bleaching agent composition in a total amount of from about 0.5 to about 15% by weight, preferably from about 1 to about 10% by weight, more preferably from about 4 to about 8% by weight, based on the total weight of the bleaching agent composition.

Cosmetic agent as contemplated herein, may include at least one thickening agent that is a mixture of a cellulose gum, a hydroxyethyl cellulose and a xanthan gum, wherein preferably the amount of cellulose gum is from about 1 to about 5% by weight, preferably from about 1.5 to about 3% by weight, the amount of xanthan gum is from about 1 to about 6% by weight, preferably from about 2 to about 4% by weight, and/or the amount of hydroxyethyl cellulose is from about 1 to about 5% by weight, preferably from about 1.5 to about 4% by weight, in each case based on the total weight of bleaching agent composition.

Blonding agent as contemplated herein, may include at least one oil that is present in a total amount of from about 0.1-80% by weight, preferably from about 2-60% by weight, more preferably from about 5 to about 40% by weight, most preferably from about 10 to about 35% by weight, in each case based on the weight of the blonding agent.

Method for lightening keratinic fibers, in particular human hair, are exemplified in that the blonding agent as contemplated herein is mixed with water, the resulting mixture applied immediately after mixing on the keratin-containing fibers, left on the fibers for about 5 to about 60 minutes and then rinsing the fibers with water and optionally washing with a surfactant-containing cleaning agent, preferably the blonding agent (B) and the liquid composition (Ox) are mixed together in a weight ratio (B):(Ox) of from about 0.2 to about 1, more preferably from about 0.3 to about 0.8, even more preferably from about 0.4 to about 0.7, most preferably from about 0.5 to about 0.6.

The statements made regarding the blonding agents as contemplated herein and preferred as contemplated herein also apply mutatis mutandis to the cosmetic products as contemplated herein and preferred as contemplated herein.

The statements made regarding the blonding agents as contemplated herein and preferred as contemplated herein also apply mutatis mutandis to the methods for lightening and/or changing the color of the keratinic fibers as contemplated herein and preferred as contemplated herein.

EXAMPLES

1. Blonding Powder Formulations
(Unless otherwise stated, amounts specified are % by weight)

|  | KM 1 | KM 2 | KM 3 |
| --- | --- | --- | --- |
| Magnesium carbonate (hard) | 12 | 22.8 | 2.6 |
| Britesil C 265 | 36.5 | 22.4 | 27 |
| Carboxymethylcellulose (Cekol 50000) | 2 | 1.9 | 2.2 |
| Hydroxyethylcellulose (Tylose H 100000 YP 2) | 2 | 1.9 | 2.3 |
| Xanthan gum (Keltrol CG-SFT) | 3.5 | 2.4 | 3.7 |
| EDETA BX Powder | 1.5 | 1.6 | 1.6 |
| Sodium persulfate | 5 | 5 | 6 |
| Ammonium persulfate + 0.5% silica | 14.5 | 10 | 14 |

-continued

|  | KM 1 | KM 2 | KM 3 |
|---|---|---|---|
| Potassium persulfate | 14.5 | 19 | 27.4 |
| Eumulgin B5 | 4.5 |  |  |
| NaCl | 0.5 | 0.5 | 0.5 |
| Dimethicone/Dimethiconol | 3 | 3 | 2.4 |
| Citric acid | 0.5 | 0.5 |  |
| L-arginine |  | 1 |  |
| Sodium percarbonate | 8 | 8 | 10 |
| Perfume |  |  | 0.3 |

The respective blonding powder and water were mixed with each other in a weight ratio of 1:2.

2. Packaging

A film from the company Safta was used for the packaging with the following data:

PET (12 μm)—Aluminium (9 μm)—PE (70 μm)

W.V.T.R. 38° C.—90% rel. hum. <0.1 g/(m²×24 h) measured with ASTM E-398

O.T.R. 23° C.—0% rel hum. <0.1 cc/(m²×24 h×bar) measured with ASTM D-3985

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A blonding agent for changing the natural color of keratinic fibers comprising a cosmetic composition (KM), wherein the cosmetic composition (KM) comprises:
   an oxidizing compound comprising a mixture of a percarbonate and one or more inorganic salts of a peroxosulphuric acid, wherein a total amount of inorganic salt of a peroxodisulfuric acid is from about 30 to about 50% by weight, based on the total weight of the blonding agent;
   a mixture of thickening agents,
   wherein the mixture of thickening agents comprises a cellulose gum, a hydroxyethyl cellulose, and a xanthan gum; and
   wherein the blonding agent is free of hydrogen peroxide.

2. The blonding agent according to claim 1, wherein the total amount of thickening agents in the blonding agent is from about 1 to about 15% by weight.

3. The blonding agent according to claim 1, wherein the thickening agent is a mixture of cellulose gum in an amount of from about 1 to about 5% by weight, of xanthan gum in an amount of from about 1 to about 6% by weight, and of hydroxyethyl cellulose in an amount of from about 1 to about 5% by weight, in each case based on the total weight of the blonding agent.

4. The blonding agent according to claim 1, further comprising at least one inorganic alkalizing agent solid at 20° C. and 10⁵ Pa, and wherein the at least one inorganic alkalizing agent includes at least one sodium silicate or sodium metasilicate having a molar $SiO_2/Na_2O$ ratio of ≥2.

5. The blonding agent according to claim 1, further comprising at least one complexing agent selected from the following acids and/or their alkali metal salts:
   ethylenediaminetetraacetic acid (EDTA); N-hydroxyethylethylenediaminetriacetic acid;
   aminotrimethylenephosphonicacid; diethylenetriaminepentaacetic acid; lauroyl ethylenediamine triacetic acid; nitrilotriacetic acid; iminodisuccinic acid;
   N-2-hydroxyethyliminodiacetic acid; ethylene glycol-bis-(beta-aminoethyl ether)-N, N-tetraacetic acid; aminotrimethylenephosphonic acid, pentasodium aminotrimethylenephosphonate, and mixtures thereof.

6. The blonding agent according to claim 1, further comprising at least one oil present in a total amount of from about 5 to about 15% by weight based on the weight of the blonding agent.

7. A cosmetic product according to claim 1, further comprising a packaging, wherein the blonding agent is included in the packaging and the packaging comprises a multilayer film (F), wherein the film (F) has a barrier layer (BS) impermeable to water vapor.

8. The blonding agent according to claim 1, wherein the total amount of thickening agents in the blonding agent is from about 6 to about 9% by weight, based on the total weight of the blonding agent.

9. The blonding agent according to claim 1, wherein the thickening agent is a mixture of cellulose gum in an amount of from about 1.5 to about 3% by weight, of xanthan gum in an amount of from about 2 to about 4% by weight, and of hydroxyethyl cellulose in an amount of from about 1.5 to about 4% by weight, in each case based on the total weight of the blonding agent.

10. The blonding agent according to claim 1, wherein the percarbonate is present in the blonding agent in a total amount of from about 2 to about 14% by weight based on the total weight of the blonding agent.

11. The blonding agent according to claim 1, wherein the percarbonate is present in the blonding agent in a total amount of from about 6 to 10% by weight based on the total weight of the blonding agent.

12. The blonding agent according to claim 1, wherein the inorganic salt of the peroxosulphuric acid is selected from sodium peroxodisulfate, potassium peroxodisulfate, ammonium peroxodisulfate, sodium peroxomonosulfate, potassium peroxomonosulfate, ammonium peroxomonosulfate, and mixtures of these inorganic salts of peroxosulfuric acid.

13. The blonding agent according to claim 5, wherein the at least one complexing agent is present in a total amount of from about 0.1 to about 1.2% by weight based on the weight of the blonding agent.

14. A blonding agent for changing the natural color of keratinic fibers, comprising a cosmetic composition (KM), wherein the cosmetic composition (KM) comprises:
   sodium peroxodisulfate, potassium peroxodisulfate, and ammonium peroxodisulfate in a total amount of from about 30 to about 50% by weight, based on the total weight of the blonding agent;
   at least one percarbonate present in the blonding agent in a total amount of from about 4 to about 12% by weight based on the total weight of the blonding agent; and
   a thickening agent comprising a mixture of cellulose gum in an amount of from about 1.5 to about 3% by weight, of xanthan gum in an amount of from about 2 to about 4% by weight, and of hydroxyethyl cellulose in an amount of from about 1.5 to about 4% by weight, in each case based on the total weight of the blonding agent, wherein the total amount of thickening agents in the blonding agent is from about 6 to about 9% by weight, based on the total weight of the blonding agent; wherein the blonding agent is free of hydrogen peroxide.

* * * * *